(12) United States Patent
Fredrick et al.

(10) Patent No.: US 11,337,815 B2
(45) Date of Patent: May 24, 2022

(54) INFLATABLE MEMBER WITH CORE MEMBERS

(71) Applicant: Boston Scientific Scimed, Inc., Maple Grove, MN (US)

(72) Inventors: Ryan Earl Fredrick, Eden Prairie, MN (US); Paul John Gindele, Buffalo, MN (US); Matthew Lee Nelson, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 85 days.

(21) Appl. No.: 16/867,081

(22) Filed: May 5, 2020

(65) Prior Publication Data
US 2020/0352721 A1   Nov. 12, 2020

Related U.S. Application Data

(60) Provisional application No. 62/845,016, filed on May 8, 2019.

(51) Int. Cl.
*A61F 2/26*   (2006.01)

(52) U.S. Cl.
CPC ........ *A61F 2/26* (2013.01); *A61F 2250/0013* (2013.01)

(58) Field of Classification Search
CPC ....................................................... A61F 2/26
See application file for complete search history.

(56) References Cited

U.S. PATENT DOCUMENTS

| 5,899,849 | A | 5/1999 | Elist et al. |
| 9,827,102 | B2 | 11/2017 | Lund et al. |
| 10,070,956 | B2 | 9/2018 | Little |
| 2005/0014993 | A1 | 1/2005 | Mische et al. |
| 2016/0081801 | A1 | 3/2016 | Little |
| 2018/0318086 | A1 | 11/2018 | Felton et al. |
| 2019/0307565 | A1* | 10/2019 | Mujwid .................... A61F 2/26 |

FOREIGN PATENT DOCUMENTS

WO   2013096615 A1   6/2013

OTHER PUBLICATIONS

International Search Report and Written Opinion for PCT Application No. PCTUS/2020/031660, dated Jul. 30, 2020, 13 pages.

* cited by examiner

*Primary Examiner* — John P Lacyk
(74) *Attorney, Agent, or Firm* — Brake Hughes Bellermann LLP

(57) ABSTRACT

According to an aspect, an inflatable implant includes a fluid reservoir configured to hold fluid; an inflatable member; and a pump assembly configured to transfer fluid from the fluid reservoir to the inflatable member, the inflatable member including a body member and a core member, the body member defining a first cavity and a second cavity, the core member being disposed within the first cavity, the second cavity being configured to receive the fluid.

15 Claims, 7 Drawing Sheets

INFLATABLE MEMBER WITH CORE MEMBERS

CROSS-REFERENCE TO RELATED APPLICATION

This application claims priority to U.S. Provisional Patent Application No. 62/845,016, filed on May 8, 2019, entitled "INFLATABLE MEMBER WITH CORE MEMBERS", the disclosure of which is incorporated by reference herein in its entirety.

TECHNICAL FIELD

This disclosure relates generally to bodily implants and more specifically to bodily implants, such as penile prosthesis that include an inflatable member.

BACKGROUND

One treatment for male erectile dysfunction is the implantation of a penile prosthesis that mechanically erects the penis. Some existing penile prostheses include inflatable cylinders or members that can be inflated or deflated using a pump mechanism. In some existing devices, the inflatable cylinder or member requires a relatively large amount of force to inflate. Additionally, in some existing devices, the pump mechanism may require many sequential squeezes or activations to inflate the cylinder or member.

Accordingly, it would be useful to provide a bodily implant, such as a penile prosthesis that includes an improved cylinder or member that can be more easily inflated.

SUMMARY

According to an aspect, an inflatable implant includes a fluid reservoir configured to hold fluid; an inflatable member; and a pump assembly configured to transfer fluid from the fluid reservoir to the inflatable member, the inflatable member including a body member and a core member, the body member defining a first cavity and a second cavity, the core member being disposed within the first cavity, the second cavity being configured to receive the fluid.

In some embodiments, the body member has a first softness, the core member has a second softness, the first softness being different than the first softness. In some embodiments, the body member has a first softness, the core member has second softness, the second softness being greater than the first softness.

In some embodiments, the first cavity is fluidically isolated from the second cavity. In some embodiments, the inflatable member has a first end portion and second end portion, the second cavity extends from a location proximate the first end portion to a location proximate the second end portion. In some embodiments, the first cavity extends in a first direction, the second cavity extends in a second direction, the first direction is substantially parallel to the second direction.

In some embodiments, the core member is a first core member, the body member defines a third cavity and a fourth cavity, the body member includes a second core member, the second core member being disposed within the third cavity, the fourth cavity being configured to receive the fluid. In some embodiments, the core member is a first core member, the body member defines a third cavity and a fourth cavity, the body member includes a second core member, the second core member being disposed within the third cavity, the fourth cavity being configured to receive the fluid, the first cavity extends substantially parallel to the second cavity, the third cavity, and the fourth cavity.

In some embodiments, the inflatable member is an elongate member. In some embodiments, the first cavity has a substantially circular cross-sectional shape. In some embodiments, the first cavity has an elongated cross-sectional shape. In some embodiments, the first cavity has an elongated and curved cross-sectional shape, the second cavity has a circular cross-sectional shape.

In some embodiments, the inflatable member defines a longitudinal axis, the first cavity being aligned along the longitudinal axis, the second cavity being offset from the longitudinal axis. In some embodiments, the inflatable member defines a longitudinal axis, the second cavity being aligned along the longitudinal axis, the first cavity being offset from the longitudinal axis.

In some embodiments, the core member is a first core member, the body member defines a third cavity, the body member includes a second core member, the second core member being disposed within the third cavity. In some embodiments, the body member defines a third cavity, the third cavity being configured to receive the fluid.

According to another aspect, an inflatable implant includes a fluid reservoir configured to hold fluid; an inflatable member; and a pump assembly configured to transfer fluid from the fluid reservoir to the inflatable member, the inflatable member including a body member and a core member, the body member defining a plurality of cavities configured to receive the fluid, the core member being softer than the body member.

In some embodiments, the core member extends in a first direction, a first of the plurality of cavities extends in a second direction, the first direction being substantially parallel to the second direction.

According to another aspect, an inflatable implant includes a fluid reservoir configured to hold fluid; an inflatable member; and a pump assembly configured to transfer fluid from the fluid reservoir to the inflatable member, the inflatable member including a body member and a core member, the body member defining a cavity, the core member being disposed within the cavity of the body member, the core member defining a cavity, the cavity of the core member being configured to receive the fluid.

In some embodiments, the cavity of the body member is configured to receive the fluid.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. For example, in some embodiments, the bodily implant is configured to be disposed within a pelvic region of a patient. For example, the bodily implant may be a penile implant. In other embodiments, the implant is configured to be disposed within a different portion of the body of the patient. The term patient or user may hereafter be used for a person who benefits from the medical device or the methods disclosed in the present disclosure. For example, the patient can be a person whose body is implanted with the medical device.

Figure 1:
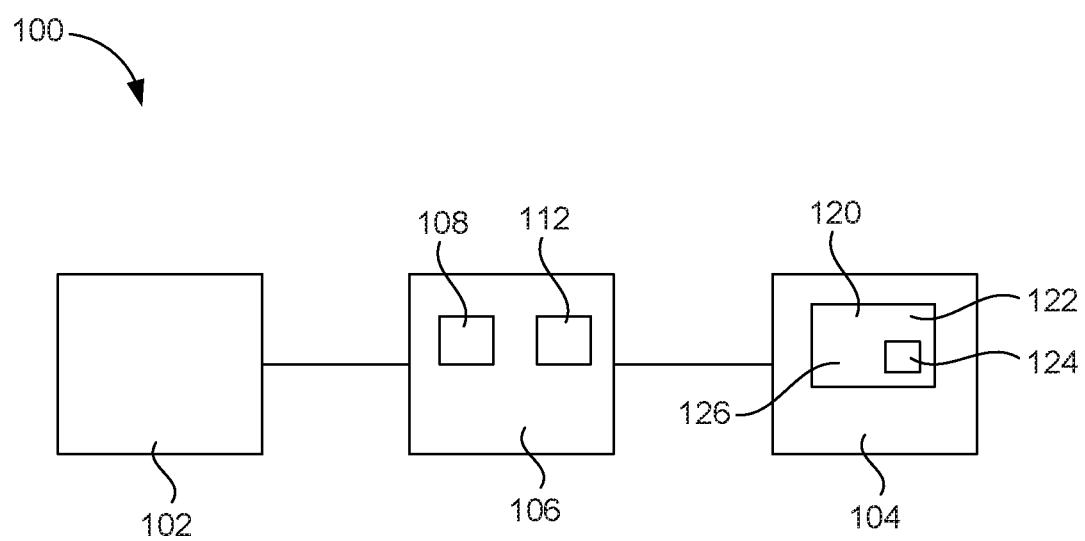
FIG. 1 schematically illustrates an inflatable implant according to an embodiment.

FIG. 1 schematically illustrates a bodily implant 100. In the illustrated embodiment, the implant is an inflatable bodily implant. The bodily implant includes a fluid reservoir 102, an inflatable member 104, and a pump assembly 106. The fluid reservoir 102 is operatively coupled to the pump assembly 106 and the pump assembly 106 is operatively coupled to the inflatable member 104. The pump assembly 106 is configured to transfer fluid between the fluid reservoir 102 and the inflatable member 104 according to an aspect.

In some embodiments, the implant 100 is a penile implant. In some such embodiments, the inflatable member 104 may be implanted into the corpus cavernosae of the user, the fluid reservoir 102 may be implanted in the abdomen or pelvic cavity of the user (e.g., the fluid reservoir 102 may be implanted in the lower portion of the user's abdominal cavity or the upper portion of the user's pelvic cavity), and the pump assembly 106 may be implanted in the scrotum of the user.

The pump assembly 106 includes a pump bulb 108 and an actuator or a deflation mode actuator 112. In an inflation mode, the user may operate the pump bulb 108 (e.g., squeeze the pump bulb 108, release, then squeeze again, etc.) to transfer fluid from the fluid reservoir 102 to the pump assembly 106, and from the pump assembly 106 to the inflatable member 104 such that a desired rigidity is achieved in the inflatable member 104. In order to deflate the inflatable member 104, the user may locate the deflation mode actuator 112, and activate the deflation mode actuator 112 to place the implant 100 in a deflation mode.

In some embodiments, the deflation mode actuator 112 is movably coupled to a pump assembly or a valve body. In some examples, the deflation mode actuator 112 includes a protrusion, that when pressed, causes the valve body to define a fluid passageway from the inflatable member 104 to the fluid reservoir 102 in order to deflate the inflatable member 104. In some examples, the deflation mode actuator 112 includes a push rod or button. In some examples, the user presses the deflation mode actuator 112 once (e.g., does not need to hold the deflation mode actuator 112) to cause fluid to drain from the inflatable member 104.

The pump bulb 108 may be a flexible member defining a cavity. In some embodiments, the pump bulb 108 is coupled to and extends from the valve body. The pump bulb 108 may be a squeeze pump. The pump bulb 108 may use suction and pressure to move the fluid in and out of the cavity of the pump bulb 108 in the inflation mode. For example, the user may depress or squeeze the pump bulb 108 to expel the fluid out of the cavity, and, when the flexible member returns to its original shape, the resulting suction pushes the fluid into the cavity of the pump bulb 108. In some examples, the pump bulb 108 may have a bulb spring rate that is designed to refill the pump bulb 108 in a selected time frame.

In the illustrated embodiment, the inflatable member 104 includes a body member 120 and a core member 122. The body member 120 includes or defines a first cavity 124 and a second cavity 126. In some embodiments, the core member 122 is disposed within the first cavity 124. The second cavity 126 is configured to receive the fluid. For example, in some embodiments, in the inflation mode, the pump bulb 108 may be activated or squeezed to transfer the fluid to the second cavity 126 of the body member 108 to inflate the inflatable member 104.

In some embodiments, the core member 122 has a softness that is greater than the softness of the body member 120. In other words, the core member 122 is softer or more flexible than the body member 120. For example, in some embodiments, the core member 122 may be of a durometer that is lower (or softer, or more flexible) than the durometer of the body member 120. In some embodiments, core member 122 is formed of a material that is softer than the material that forms the body member 120. In other embodiments, the core member 122 is formed of the same material as the body member 120.

In some embodiments, the inflatable member 104 includes more than one core member. For example, in some embodiments, the inflatable member 104 includes two, three, four, or more core members.

In some embodiments, the first cavity 124 is separate or disposed apart from the second cavity 126. In some embodiments, the first cavity 124 is fluidically isolated from the second cavity 126.

In some embodiments, the combination of the body member 120 and the core member 122 allow or help facilitate the inflation of the inflatable member. For example, in some embodiments, the user may inflate the inflatable member by actuating the pump bulb fewer times. Additionally, in some embodiments, the body member and the core member may help retain the inflatable member in a cylindrical shape when the inflatable member is in its deflated configuration (rather than a flat or semi-planar shape).

Figure 2:
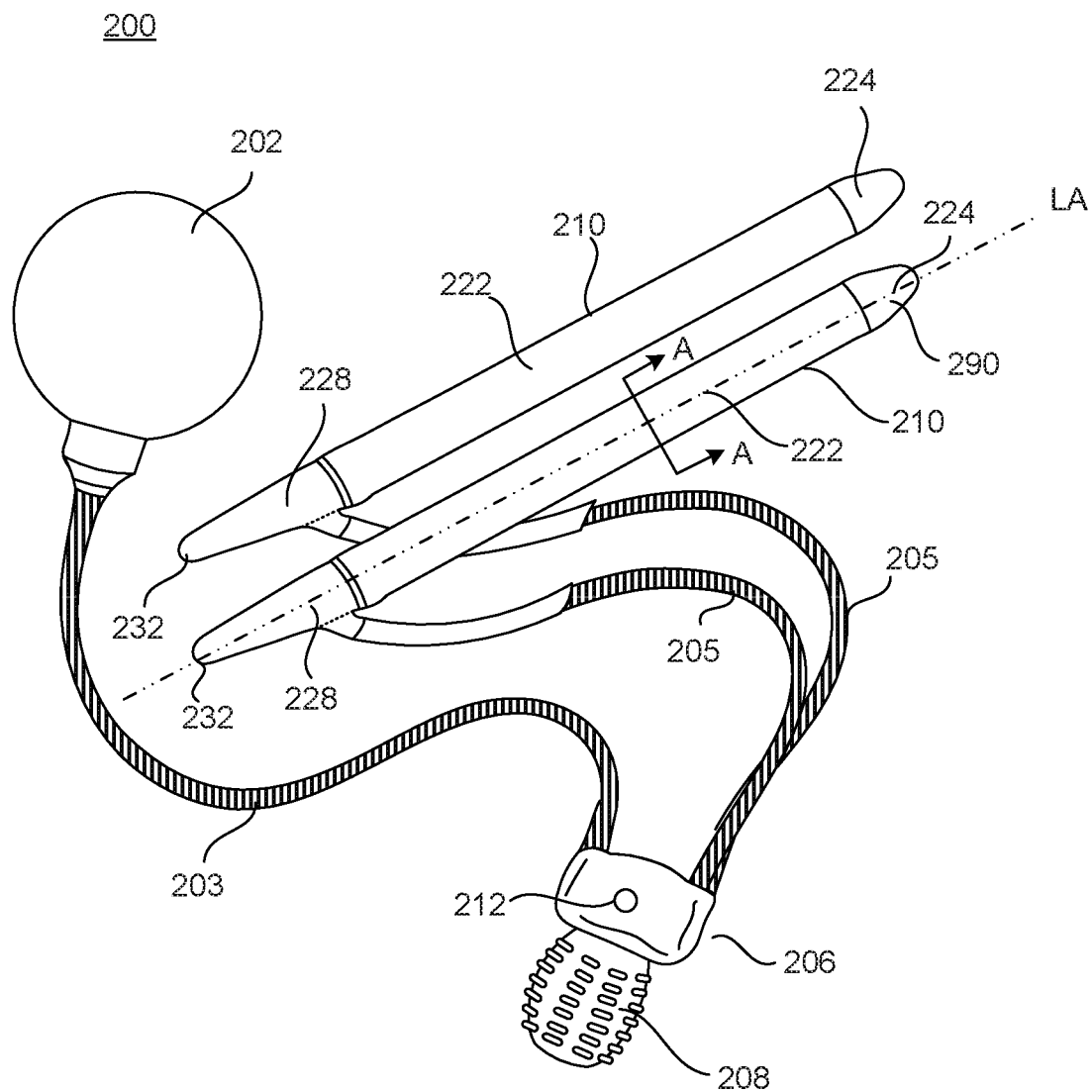
FIG. 2 illustrates an inflatable penile implant according to an embodiment.

FIG. 2 illustrates an inflatable penile prosthesis or implant 200 having a pump assembly 206 according to an aspect. The penile prosthesis 200 may include a pair of inflatable cylinders 210, and the inflatable cylinders 210 are configured to be implanted in a penis of the patient. For example, one of the inflatable cylinders 210 may be disposed on one side of the penis, and the other inflatable cylinder 210 may be disposed on the other side of the penis. Each inflatable cylinder 210 may include a first end portion 224, a cavity or inflation chamber 222, and a second end portion 228 having a rear tip 232.

The pump assembly 206 may be implanted into the patient's scrotum. A pair of conduit connectors 205 may attach the pump assembly 206 to the inflatable cylinders 210 such that the pump assembly 206 is in fluid communication with the inflatable cylinders 210. Also, the pump assembly 206 may be in fluid communication with a fluid reservoir 202 via a conduit connector 203. The fluid reservoir 202 may be implanted into the user's abdomen. The inflation chamber or portion 222 of the inflatable cylinder 210 may be disposed within the penis. The first end portion 224 of the inflatable cylinder 210 may be at least partially disposed within the crown portion of the penis. The second end portion 228 may be implanted into the patient's pubic region with the rear tip 232 proximate the pubic bone.

In order to implant the inflatable cylinders 210, the surgeon may first prepare the patient. The surgeon often makes an incision in the penoscrotal region, e.g., where the base of the penis meets with the top of the scrotum. From the penoscrotal incision, the surgeon may dilate the patient's corpus cavernosae to prepare the patient to receive the inflatable cylinders 210. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 228. The surgeon may measure the length of the corpora cavernosae from the incision and the dilated region of the pubic area to determine an appropriate size of the inflatable cylinders 210 to implant.

After the patient is prepared, the penile prosthesis 200 is implanted into the patient. The tip of the first end portion 224 of each inflatable cylinder 210 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the inflatable cylinder 210 into the corpus cavernosum. This is done for each inflatable cylinder 210 of the pair. Once the inflation chamber 222 is in place, the surgeon may remove the suture from the tip. The surgeon then inserts the second end portion 228. The surgeon inserts the rear end of the inflatable cylinder 210 into the incision and forces the second end portion 228 toward the pubic bone until each inflatable cylinder 210 is in place.

A pump bulb 208 of the pump assembly 206 may be squeezed or depressed by the user in order to facilitate the transfer of fluid from the fluid reservoir 202 to the inflatable cylinders 210. For example, in the inflation mode, while the user is operating the pump bulb 208, the pump bulb 208 may receive the fluid from the fluid reservoir 202, and then output the fluid to the inflatable cylinders 210. When the user switches to the deflation mode, at least some of the fluid can automatically be transferred back to the fluid reservoir 202 (due to the difference in pressure from the inflatable cylinders 210 to the fluid reservoir 202). Then, the user may squeeze the inflatable cylinders 210 to facilitate the further transfer of fluid through the pump bulb 208 to the fluid reservoir 202.

In the illustrated embodiment, the pump assembly 206 includes an actuation member 212. The actuation member 212 may be used by the patient to toggle or switch the penile implant 200 from its inflate mode to its deflate mode.

Figure 3:
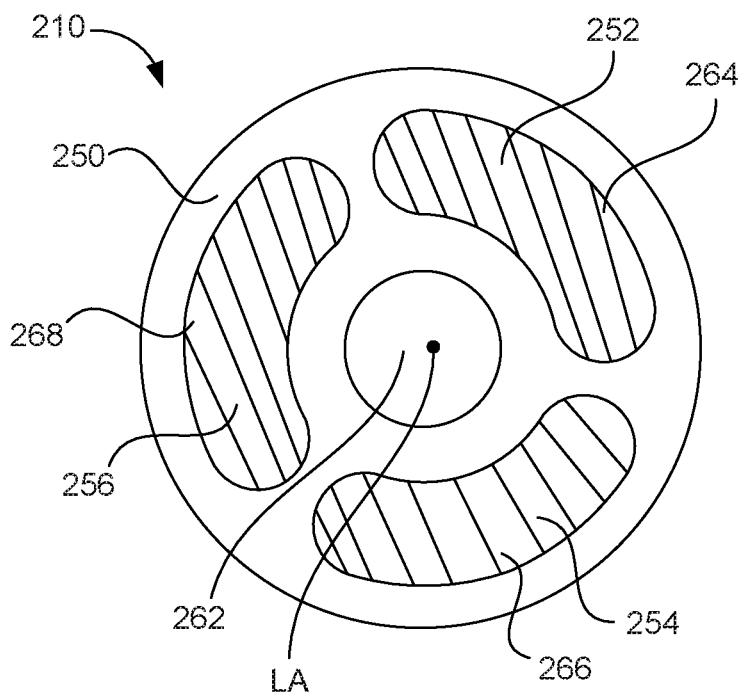
FIG. 3 is a cross-sectional view of the inflatable member of the penile implant of FIG. 2 taken along line A-A.

FIG. 3 is a cross-sectional view of the inflatable cylinder or member 210 taken along line A-A of FIG. 2. In the illustrated embodiment, the inflatable member 210 includes a body member 250 and core members 252, 254, and 256. The body member 250 includes or defines a first cavity 262, a second cavity 264, a third cavity 266, and a fourth cavity 268. The core members 252, 254, and 256 are disposed in the second, third, and fourth cavities. The first cavity 262 is configured to receive the fluid. For example, in some embodiments, in the inflation mode, the pump bulb 208 may be activated or squeezed to transfer the fluid to the first cavity 262 of the body member 250 to inflate the inflatable member 210.

The core members 252, 254, and 256 have a softness that is greater than the softness of the body member 250. In other words, the core members 252, 254, and 256 are softer or more flexible than the body member 250. For example, in some embodiments, the core members 252, 254, 256 may be of a durometer that is lower (or softer, or more flexible) than the durometer of the body member 250. In some embodiments, core members are formed of a material that is softer than the material that forms the body member. In other embodiments, the core members are formed of the same material as the body member. For example, in one embodiment, the body member and the core member are formed of a silicone material.

In the illustrated embodiment, the cavities 262, 264, 266, and 268 extend along the length of the inflatable member 210. In some embodiments, the cavities 262, 264, 266, and 268 extend from a first end portion of the inflatable member 210 to a second end portion of the inflatable member 210. In the illustrated embodiment, the cavities are disposed apart from each other. In other words, the cavities 262, 264, 266, and 268 are fluidically isolated from each other.

In the illustrated embodiment, the first cavity 262 is disposed along the longitudinal axis LA of the body member 250. The other cavities 264, 266, and 268 are disposed around the longitudinal axis. In the illustrated embodiment, the first cavity 262 has a circular cross-section. The other cavities 264, 266, and 268 have elongated and curved cross-sectional shapes.

In some embodiments, the combination of the body member 250 and the core members 252, 254, and 256 allow or help facilitate the inflation of the inflatable member. For example, in some embodiments, the user may inflate the inflatable member by actuating the pump bulb fewer times. Additionally, the inflatable member may tend towards a cylindrical shape when in the deflated configuration rather than a flat shape.

Figure 4:
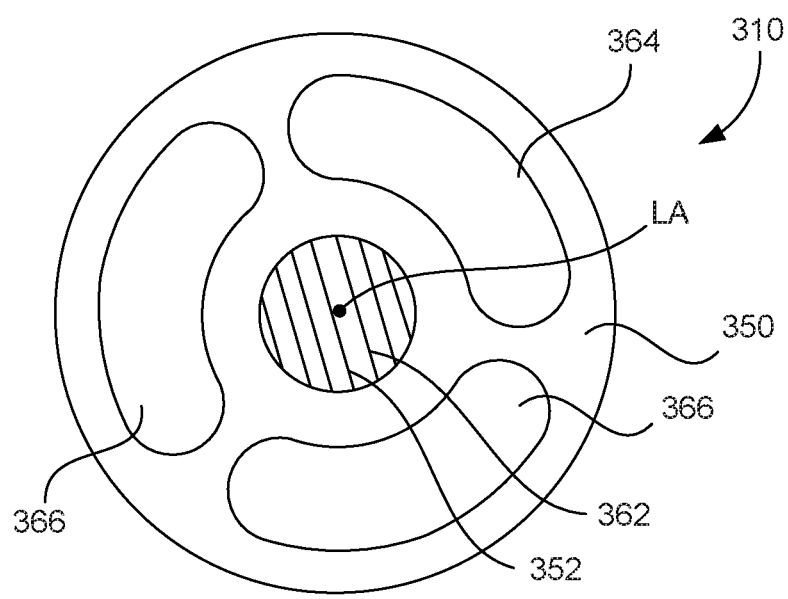
FIGS. 4-8 are cross-sectional views of inflatable members according to embodiments.

FIG. 4 is a cross-sectional view of an inflatable cylinder or member according to an embodiment. In the illustrated embodiment, the inflatable member 310 includes a body member 350 and a core member 252. The body member 350 includes or defines a first cavity 362, a second cavity 364, a third cavity 366, and a fourth cavity 368. The core member 352 is disposed in the first cavity 362. The other cavities 364, 366, and 368 are configured to receive the fluid. For example, in some embodiments, in the inflation mode, the pump bulb may be activated or squeezed to transfer the fluid to the cavities 364, 366, 368 of the body member 350 to inflate the inflatable member 310.

The core member 352 has a softness that is greater than the softness of the body member 350. In other words, the core member 352 is softer or more flexible than the body member 350. For example, in some embodiments, the core member 352 may be of a durometer that is greater (or softer, or more flexible) than the durometer of the body member 350. In some embodiments, core member is formed of a material that is softer than the material that forms the body member. In other embodiments, the core member is formed of the same material as the body member. For example, in one embodiment, the body member and the core member are formed of a silicone material.

In the illustrated embodiment, the cavities 362, 364, 366, and 368 extend along the length of the inflatable member 310. In some embodiments, the cavities 362, 364, 366, and 368 extend from a first end portion of the inflatable member 310 to a second end portion of the inflatable member 310. In the illustrated embodiment, the cavities are disposed apart from each other. In other words, the cavities 362, 364, 366, and 368 are fluidically isolated from each other.

In the illustrated embodiment, the first cavity 362 is disposed along the longitudinal axis LA of the body member 350. The other cavities 364, 366, and 368 are disposed around the longitudinal axis. In the illustrated embodiment, the first cavity 362 has a circular cross-section. The other cavities 364, 366, and 368 have elongated and curved cross-sectional shapes.

In some embodiments, the combination of the body member 350 and the core member 352 allow or help facilitate the inflation of the inflatable member. For example, in some embodiments, the user may inflate the inflatable member by actuating the pump bulb fewer times. Additionally, the inflatable member may tend towards a cylindrical shape when in the deflated configuration rather than a flat shape.

Figure 5:
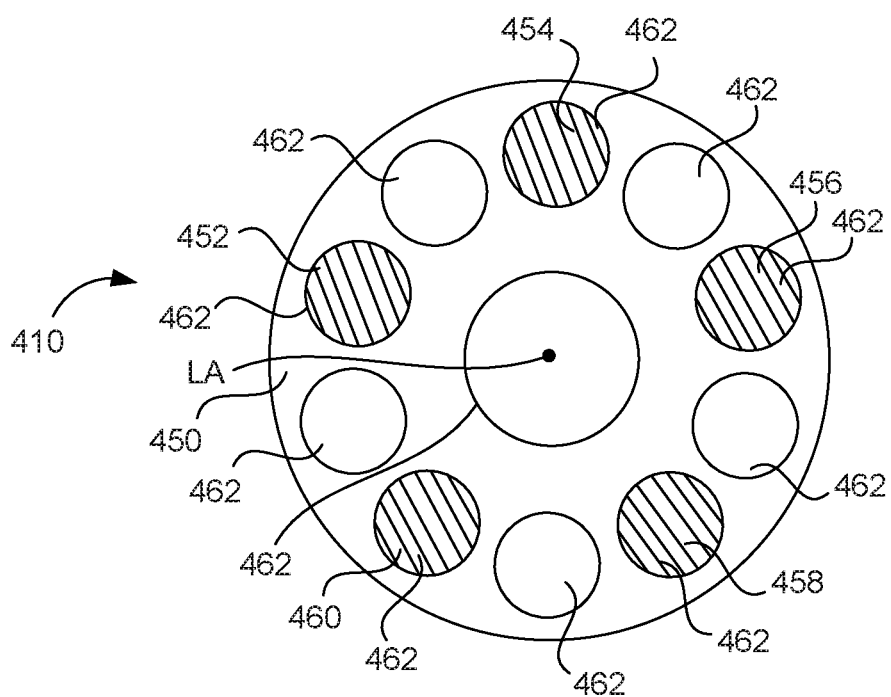

FIG. 5 is a cross-sectional view of an inflatable cylinder or member 410 according to an embodiment. In the illustrated embodiment, the inflatable member 410 includes a body member 450 and core members 452, 454, 456, and 458. The body member 450 includes or defines a plurality of cavities 462. The core members 452, 454, 456, and 458 are disposed in some of the cavities. Some of the cavities are configured to receive the fluid. For example, in some embodiments, in the inflation mode, the pump bulb may be activated or squeezed to transfer the fluid to the cavities of the body member 450 to inflate the inflatable member 410.

The core members 452, 454, 456, and 458 have a softness that is greater than the softness of the body member 450. In other words, the core members 452, 454, 456, and 458 are softer or more flexible than the body member 450. For example, in some embodiments, the core members 452, 454, 456, and 458 may be of a durometer that is lower (or softer, or more flexible) than the durometer of the body member 450. In some embodiments, core members are formed of a material that is softer than the material that forms the body member. In other embodiments, the core members are formed of the same material as the body member. For example, in one embodiment, the body member and the core member are formed of a silicone material.

In the illustrated embodiment, the cavities 462 extend along the length of the inflatable member 410. In some embodiments, the cavities 462 extend from a first end portion of the inflatable member 410 to a second end portion of the inflatable member 410. In the illustrated embodiment, the cavities are disposed apart from each other. In other words, the cavities 462 are fluidically isolated from each other.

In the illustrated embodiment, the one of the cavities is disposed along the longitudinal axis LA of the body member 450. The cavity that is disposed along the longitudinal axis LA is one of the cavities that is configured to receive the fluid. The other cavities are disposed around the longitudinal axis LA. In the illustrated embodiment, cavities have a circular cross-section.

In some embodiments, the combination of the body member 450 and the core members allow or help facilitate the inflation of the inflatable member. For example, in some embodiments, the user may inflate the inflatable member by actuating the pump bulb fewer times. Additionally, the inflatable member may tend towards a cylindrical shape when in the deflated configuration rather than a flat shape.

Figure 6:
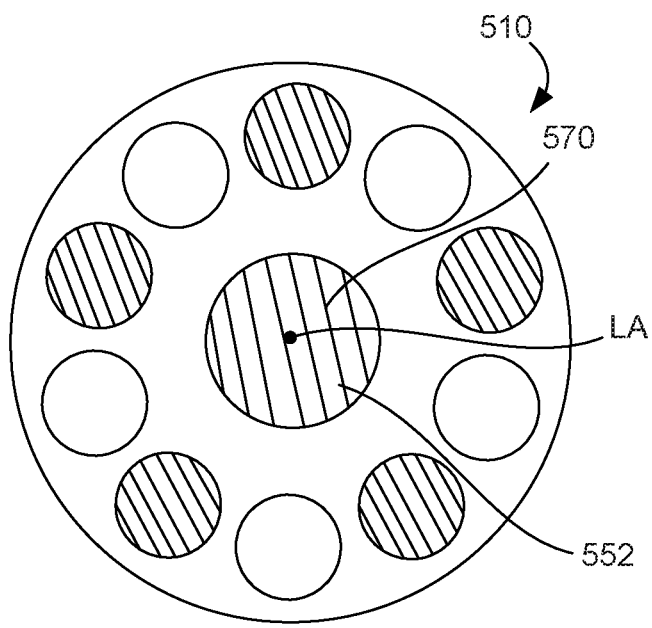

FIG. 6 is a cross-sectional view of an inflatable cylinder or member 510 according to an embodiment. In the illustrated embodiment, the inflatable member 510 is similar to inflatable cylinder or member 510, however in this embodiment a core member 552 is disposed within the cavity 570 that extends along the longitudinal axis LA.

Figure 7:
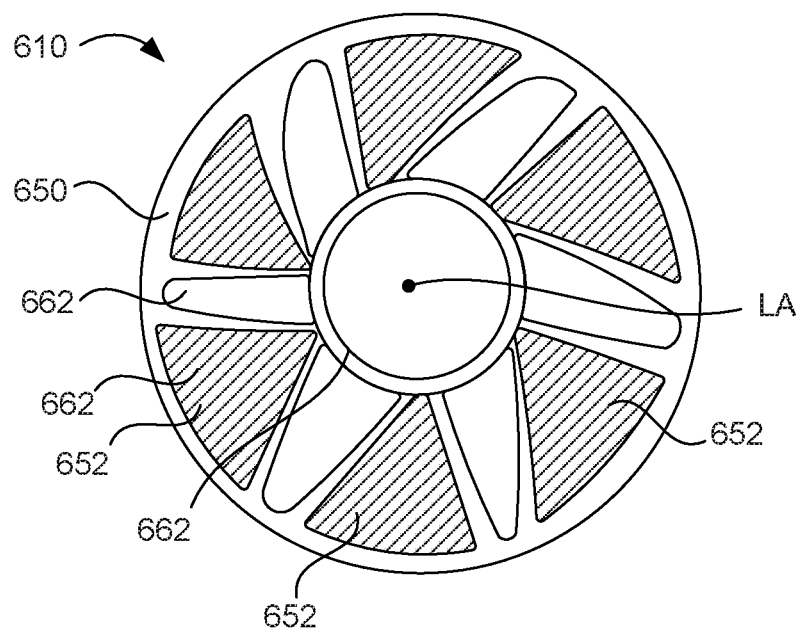

FIG. 7 is a cross-sectional view of an inflatable cylinder or member 610 according to an embodiment. In the illustrated embodiment, the inflatable member 610 includes a body member 650 and core members 652. The body member 650 includes or defines a plurality of cavities 662. The core members 652 are disposed in some of the cavities. Some of the cavities are configured to receive the fluid. For example, in some embodiments, in the inflation mode, the pump bulb may be activated or squeezed to transfer the fluid to the cavities of the body member 650 to inflate the inflatable member 610.

The core members 652 have a softness that is greater than the softness of the body member 650. In other words, the core members 652 are softer or more flexible than the body member 650. For example, in some embodiments, the core members 652 may be of a durometer that is greater (or softer, or more flexible) than the durometer of the body member 650. In some embodiments, core members 650 are formed of a material that is softer than the material that forms the body member 652. In other embodiments, the core members are formed of the same material as the body member. For example, in one embodiment, the body member and the core member are formed of a silicone material.

In the illustrated embodiment, the cavities 662 extend along the length of the inflatable member 610. In some embodiments, the cavities 662 extend from a first end portion of the inflatable member 610 to a second end portion of the inflatable member 610. In the illustrated embodiment, the cavities are disposed apart from each other. In other words, the cavities 662 are fluidically isolated from each other.

In the illustrated embodiment, the one of the cavities is disposed along the longitudinal axis LA of the body member 650. The cavity that is disposed along the longitudinal axis LA is one of the cavities that is configured to receive the fluid. The other cavities are disposed around the longitudinal axis LA. In the illustrated embodiment, the central cavity has a circular cross-section and the other cavities have irregular shaped cross-sectional shapes.

In some embodiments, the combination of the body member 650 and the core members allow or help facilitate the inflation of the inflatable member. For example, in some embodiments, the user may inflate the inflatable member by actuating the pump bulb fewer times. Additionally, the inflatable member may tend towards a cylindrical shape when in the deflated configuration rather than a flat shape.

Figure 8:
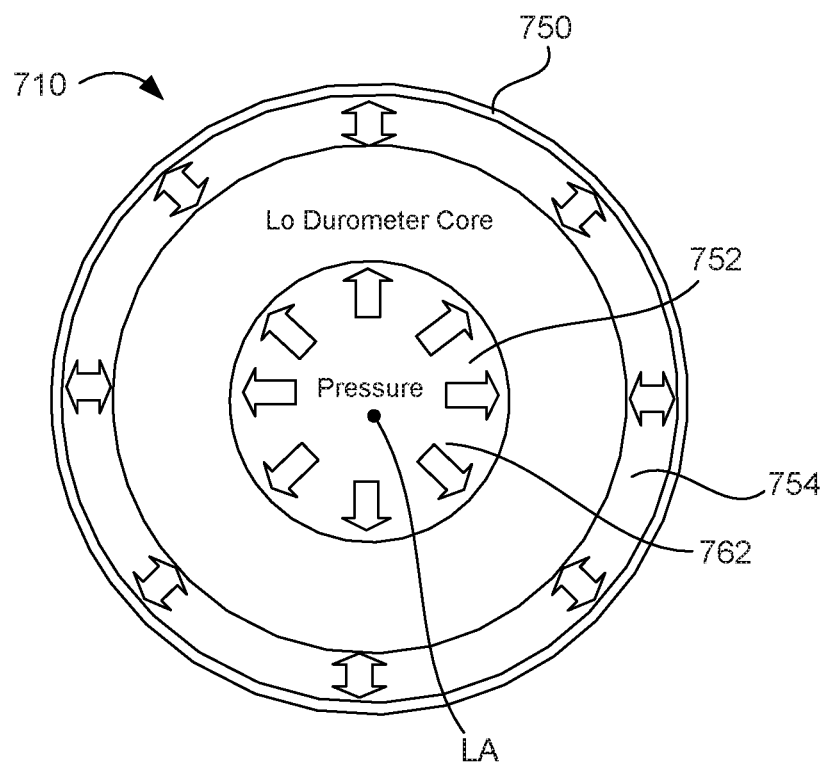
Figure 9:
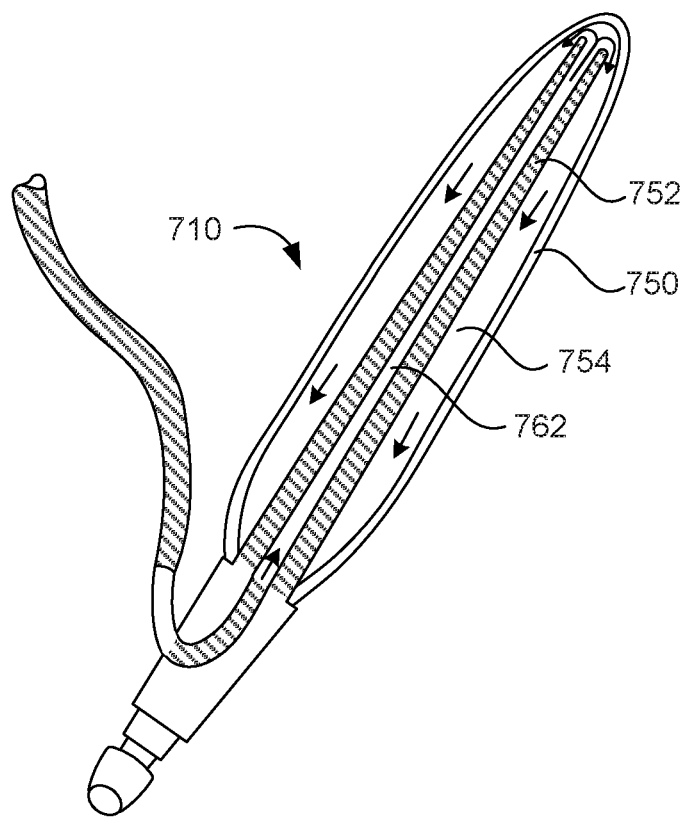
FIG. 9 is a cross-sectional view of the inflatable member of FIG. 8.

FIGS. 8-12 illustrate an inflatable cylinder or member 710 according to an embodiment. FIGS. 8 and 9 are cross-sectional views of the inflatable cylinder or member 710 according to an embodiment. In the illustrated embodiment, the inflatable member 710 includes a body member 750 and a core member 752. The body member 750 includes or defines a cavity 762. The core member 752 is disposed within the cavity 762. In the illustrated embodiment, the core member 752 defines a cavity 754. The cavity 754 and the cavity 762 are configured to receive the fluid. For example, in some embodiments, in the inflation mode, the pump bulb may be activated or squeezed to transfer the fluid to the cavities of the body member 750 to inflate the inflatable member 710.

The core member 752 has a softness that is greater than the softness of the body member 750. In other words, the core member 752 is softer or more flexible than the body member 750. For example, in some embodiments, the core member 752 may be of a durometer that is lower (or softer, or more flexible) than the durometer of the body member 750. In some embodiments, core member 752 is formed of a material that is softer than the material that forms the body member 750. In other embodiments, the core member is formed of the same material as the body member. In some embodiments, the body member 750 is formed of a fabric material.

In the illustrated embodiment, the core member 752 is disposed along the longitudinal axis LA of the body member 750. Accordingly, in some embodiments, the cavity 754 extends along the longitudinal axis LA. In some embodiments, the core member 752 is coupled to the inflatable member (for example, at a first end portion or at a second end portion of the inflatable member). In such embodiments, the core member is configured to remain in its position within the cavity 762.

In the illustrated embodiment, the cavities 762 and 754 extend coaxially with each other.

Figure 10:
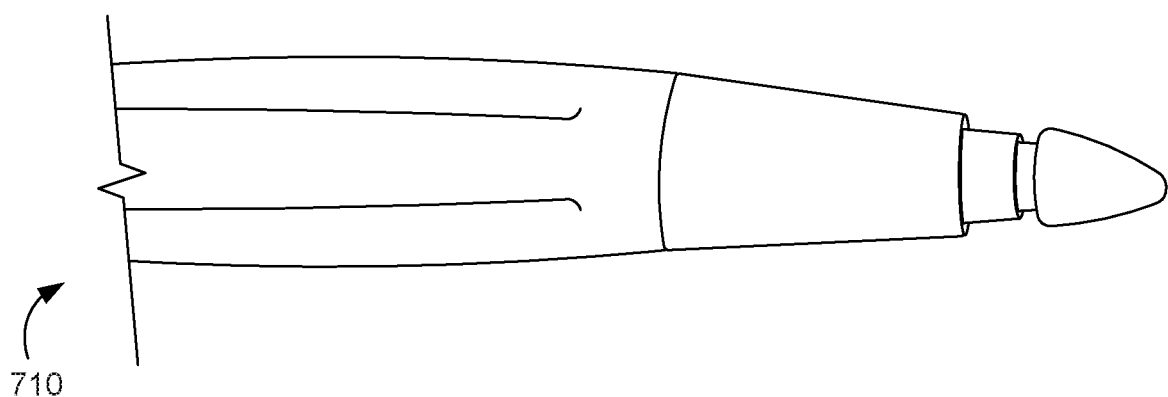
FIGS. 10 and 11 are side views of the inflatable member of FIG. 8.
Figure 11:
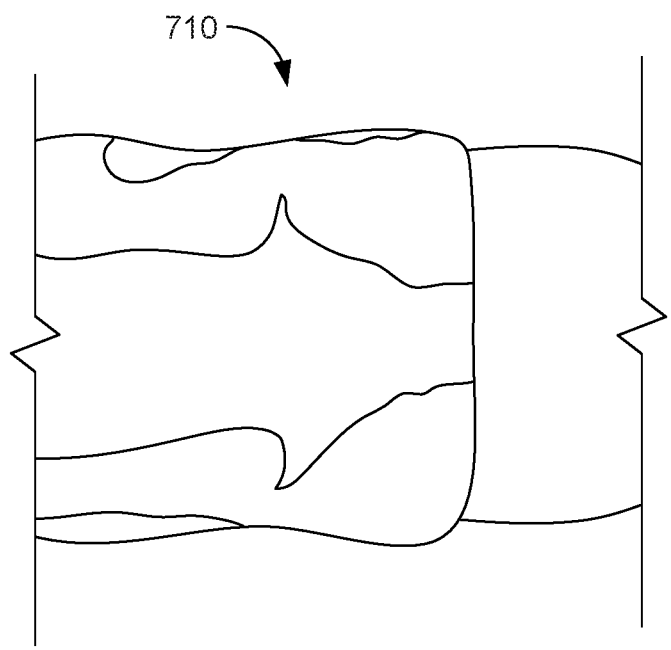
Figure 12:
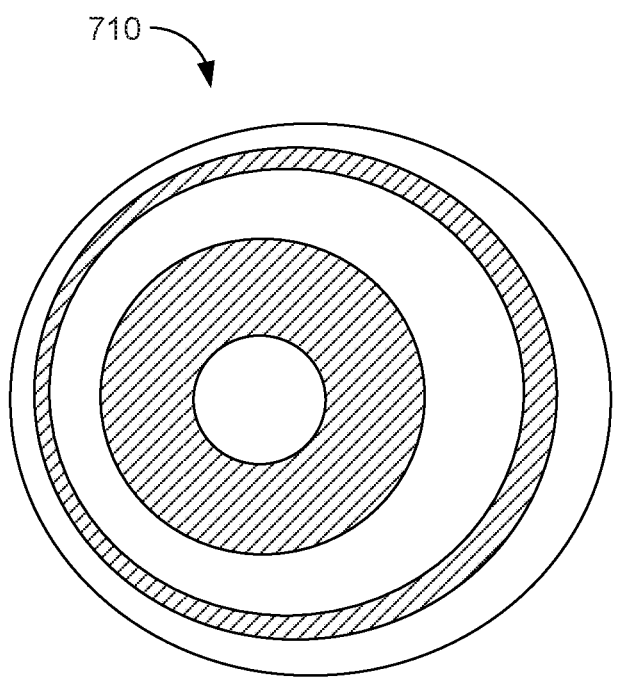
FIG. 12 is a cross-sectional view of the inflatable member of FIG. 8.

As best illustrated in FIG. 9, the cavity 762 is fluidically coupled to the cavity 754. FIGS. 10 and 11 illustrate an end portion of the inflatable member 710. FIG. 12 is a cross-sectional view of the inflatable member 710.

In some embodiments, the combination of the body member 750 and the core members allow or help facilitate the inflation of the inflatable member. For example, in some embodiments, the user may inflate the inflatable member by actuating the pump bulb fewer times. Additionally, the inflatable member may tend towards a cylindrical shape when in the deflated configuration rather than a flat shape.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable implant, comprising:
 a fluid reservoir configured to hold fluid;
 an inflatable member; and
 a pump assembly configured to transfer fluid from the fluid reservoir to the inflatable member,
 the inflatable member including a body member, a first core member, and a second core member, the body member defining a first cavity, a second cavity, and a third cavity, the first core member being disposed within the first cavity, the second core member being disposed within the third cavity, the second cavity being configured to receive the fluid, the first cavity having an elongated and curved cross-sectional shape, the third cavity having an elongated and curved cross-sectional shape, the second cavity having a round cross-sectional shape.

2. The inflatable implant of claim 1, wherein the body member has a first softness, the first core member has a second softness, the first softness being different than the first softness.

3. The inflatable implant of claim 1, wherein the body member has a first softness, the first core member has second softness, the second softness being greater than the first softness.

4. The inflatable implant of claim 1, wherein the first cavity is fluidically isolated from the second cavity.

5. The inflatable implant of claim 1, wherein the inflatable member has a first end portion and second end portion, the second cavity extends from a location proximate the first end portion to a location proximate the second end portion.

6. The inflatable implant of claim 1, wherein the first cavity extends in a first direction, the second cavity extends in a second direction, the first direction is substantially parallel to the second direction.

7. The inflatable implant of claim 1, wherein the body member defines a fourth cavity configured to receive the fluid.

8. The inflatable implant of claim 1, wherein the body member defines a fourth cavity configured to receive the fluid, the first cavity extends substantially parallel to the second cavity, the third cavity, and the fourth cavity.

9. The inflatable implant of claim 1, wherein the inflatable member is an elongate member.

10. The inflatable implant of claim 1, wherein the inflatable member defines a longitudinal axis, the first cavity being aligned along the longitudinal axis, the second cavity being offset from the longitudinal axis.

11. The inflatable implant of claim 1, wherein the inflatable member defines a longitudinal axis, the second cavity being aligned along the longitudinal axis, the first cavity being offset from the longitudinal axis.

12. An inflatable implant, comprising:
 a fluid reservoir configured to hold fluid;
 an inflatable member; and
 a pump assembly configured to transfer fluid from the fluid reservoir to the inflatable member,
 the inflatable member including a body member, a first core member, and a second core member, the body member defining a plurality of cavities configured to receive the fluid, the first core member being softer than the body member, the first core member having an elongate and curved cross-sectional shape, the second core member having an elongate and curved cross-sectional shape.

13. The inflatable implant of claim 12, wherein the core member extends in a first direction, a first of the plurality of cavities extends in a second direction, the first direction being substantially parallel to the second direction.

14. An inflatable implant, comprising:
 a fluid reservoir configured to hold fluid;
 an inflatable member; and
 a pump assembly configured to transfer fluid from the fluid reservoir to the inflatable member,
 the inflatable member including a body member and a core member, the body member defining a cavity, the core member being disposed within the cavity of the body member, the core member defining a cavity, the cavity of the core member being configured to receive the fluid, the cavity of the core member being in fluid communication with the cavity of the body member.

15. The inflatable member of claim 14, wherein the cavity of the body member is configured to receive fluid.

* * * * *